United States Patent [19]

Flanagan et al.

[11] 4,085,123

[45] Apr. 18, 1978

[54] 1,3-DIAZIDO-2-NITRAZAPROPANE

[75] Inventors: Joseph E. Flanagan, Woodland Hills; Milton B. Frankel, Tarzana, both of Calif.

[73] Assignee: Rockwell International Corporation, El Segundo, Calif.

[21] Appl. No.: 734,495

[22] Filed: Oct. 21, 1976

[51] Int. Cl.$^2$ .......................................... C07C 117/00
[52] U.S. Cl. ................................. 260/349; 149/19.8; 149/92
[58] Field of Search ........................... 149/92; 260/349

[56] References Cited

U.S. PATENT DOCUMENTS

| | | | |
|---|---|---|---|
| 3,073,731 | 1/1963 | Cohen et al. | 149/92 |
| 3,873,579 | 3/1975 | Rosher | 149/92 X |
| 3,883,377 | 5/1975 | Wright | 149/92 X |

*Primary Examiner*—Leland A. Sebastian
*Attorney, Agent, or Firm*—L. Lee Humphries; Robert M. Sperry

[57] ABSTRACT

1,3-Diazido-2-nitrazapropane, is disclosed as an energetic plasticizer, together with a method for producing same.

2 Claims, No Drawings

1,3-DIAZIDO-2-NITRAZAPROPANE

BACKGROUND OF THE INVENTION

1. Field of the Invention

This invention relates to compositions of matter and methods for producing same and is particularly directed to the disclosure of a liquid organic nitramine compound, containing two azide groups, as an energetic plasticizer, together with a method for producing this compound.

2. Description of the Prior Art

Solid propellants are formulated from a fuel and an oxidizer, together with various additives for modifying the physical or chemical properties of the propellant. In addition, there is a continuing search for materials which can yield greater energy. Following this line of thinking, U.S. Pat. No. 3,883,374 teaches a process for producing a plurality of energetic compounds having the formula

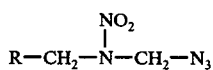

where R represents H or

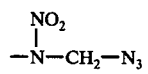

or an alkyl group of 1 to 6 carbon atoms or an alkyl group of 1 to 6 carbon atoms with at least one hydrogen atom has been replaced by the group

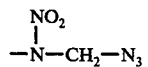

to form a group of the formula

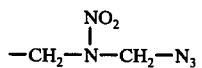

The replacement of R in equation (1) by another $N_3$ would be most desirable, since $N_3$ is much more energetic than any of the R substitutes taught by the patent. Unfortunately, all prior attempts to provide an $N_3$ substitute for R in equation (1) have been unsuccesful.

Brief Summary and Objects of the Invention

The disadvantages of the prior art are overcome with the present invention and 1,3-diazido-2-nitrazapropane (DANP) is provided, having the formula

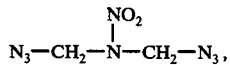

for use as an energetic plasticizer in solid propellants, together with a method of producing DANP.

Accordingly, it is an object of the present invention to provide improved materials for formulating solid propellants, together with a process for producing same.

Another object of the present invention is to provide a new composition of matter, together with a method for producing same.

An additional object of the present invention is to provide an energetic plasticizer composition, together with a method for producing same.

A further object of the present invention is to provide 1,3-diazido-2-nitrazapropane (DANP), together with a method for producing same.

These and other objects and features of the present invention will be apparent from the following detailed description.

Detailed Description of the Invention

The present invention relates to a novel azide plasticizer and to a process for producing same. The azide plasticizer of this invention can be prepared as follows:

A 12-liter, 3-necked flask, fitted with a mechanical stirrer, thermometer, and dropping funnel was charged with 3840 ml (40.7 moles) of acetic anhydride and cooled to 0°–10° C. Maintaining the temperature at 0°–10° C with external cooling, 1440 ml (34.3 moles) of 99% nitric acid was added in 30 minutes. A solution of 949 grams (6.77 moles) of hexamine in 1760 ml of glacial acetic acid was added in 1.5 hours at 5°–10° C. The mixture was stirred for additional five hours at ambient temperature, allowed to sit overnight. It was then filtered to separate a solid which was 1,7-diacetoxy-2,4,6-trinitrazaheptane.

The acid filtrate from the reaction mixture was diluted with 1500 ml of methylene chloride and washed with water, 16% sodium hydroxide, water, dried and concentrated to give a crude liquid residue consisting of 1,3-diacetoxy-2-nitrazapropane (DACNP) plus an unidentified polymeric material. It was found difficult to remove the DACNP by conventional distillation. However, utilizing a high vacuum, wiped film still, the DACNP was readily distilled at 121°C/0.3mm, $n^{25}D$ 1.4552. The yield of DACNP was 332.6 grams (35.1%), based on hexamine.

A solution of 238.3 grams (1.16 moles) of DACNP and 400 ml of dioxane was saturated with anhydrous hydrogen chloride gas at 5°–15° for 1.5 hours and stored in the refrigerator for 88 hours. The solution was concentrated and distilled to give 172.6 grams (93.6%) of colorless liquid, b.p. 64 C/0.4mm, $n^{25}D$ 1.5050. The product cyrstallized on standing and was identified as 1,3-dichloro-2-nitrazapropane (DCNP).

A solution of 172.6 grams (1.09 moles) of DCNP in 500 m. of acetone was added in 30 minutes to a solution of 195 grams (3.0 moles) of sodium azide in 600 ml of water. The reaction was maintained at ambient temperature by mild cooling during the addition. The solution was stirred for three hours at ambient temperature and extracted with methylene chloride. The methylene chloride solution was washed with water, dried, and concentrated to give 160.6 grams (85.7%) of yellow liquid. Distillation of a small portion of the product gave a colorless liquid, boiling point 97 C/0.45mm, melting point −8° C, density of 1.432 grams/cc, $n_D^{23} =$ 1.5265. Elemental and infrared analysis confirmed the product to be 1,3-diazido-2-nitrazapropane (DANP).

Caution must be exercised in handling DANP due to its sensitive nature.

The comparative performance of DANP in a typical gun propellant system was analyzed and the data is given in Table A.

TABLE A

| COMPARATIVE PROPELLANT PERFORMANCE | | | |
|---|---|---|---|
| Ingredient | Weight Percent | | |
| Nitrocellulose (12.6% N) | 100.0 | 60.0 | 60.0 |
| Nitroglycerin (NG) |  | 40.0 |  |
| 1,3-Diazido-2-Nitrazapropane (DANP) |  |  | 40.0 |
| Isochoric Flame Temperature, °K | 3103 | 3875 | 3875 |
| Mass Impetus, (Ft-lbs/16m × $10^{-3}$) | 348.7 | 397.1 | 463.2 |
| Gas molecular Weight | 24.76 | 27.15 | 23.28 |

Substitution of 40 percent plasticizer (either NG or DANP) yields a flame temperature of 3875°K, but the propellant containing DANP yields 17 percent more impetus.

Obviously, numerous variations and modifications may be made without departing from the present invention. Accordingly, it should be clearly understood that the form of the present invention described above is illustrative only and is not intended to limit the scope of the present invention.

We claim:

1. An energetic plasticizer having the composition

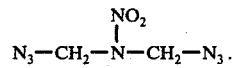

2. The method of producing the energetic plasticizer of claim 1 consisting of the steps of:
    reacting 1,3-dichloro-2-nitrazapropane with an aqueous solution of sodium azide,
    extracting said solution with methylene chloride, and
    separating the 1,3-diazido-2-nitrazapropane from the extracted solution by distillation.

UNITED STATES PATENT AND TRADEMARK OFFICE
CERTIFICATE OF CORRECTION

PATENT NO. : 4,085,123
DATED : April 18, 1978
INVENTOR(S) : Joseph E. Flanagan et al It is certified that error appears in the above-identified patent and that said Letters Patent are hereby corrected as shown below:

Column 3, TABLE A, line 9, delete "Mass Impetus, (Ft-lbs/16m X $10^{-3}$)" and insert --Mass Impetus, (Ft-lbs/1bm X $10^{-3}$)--.

Signed and Sealed this

Nineteenth Day of September 1978

[SEAL]

Attest:

RUTH C. MASON
*Attesting Officer*

DONALD W. BANNER
*Commissioner of Patents and Trademarks*